(12) United States Patent
Moss et al.

(10) Patent No.: US 9,675,406 B2
(45) Date of Patent: Jun. 13, 2017

(54) ABLATION DEVICE WITH GUIDE SLEEVES

(75) Inventors: Kevin Lee Moss, Tracy, CA (US); Meir Hai Moshe, El Sobrante, CA (US); Sravanthi Avuthu, San Jose, CA (US); Robert M. Pearson, San Jose, CA (US)

(73) Assignee: AngioDynamics, Inc.

( * ) Notice: Subject to any disclaimer, the term of this patent is extended or adjusted under 35 U.S.C. 154(b) by 1427 days.

(21) Appl. No.: 13/027,801

(22) Filed: Feb. 15, 2011

(65) Prior Publication Data

US 2011/0202053 A1    Aug. 18, 2011

Related U.S. Application Data

(60) Provisional application No. 61/304,854, filed on Feb. 16, 2010, provisional application No. 61/392,967, filed on Oct. 14, 2010.

(51) Int. Cl.
| | |
|---|---|
| *A61B 18/18* | (2006.01) |
| *A61B 18/14* | (2006.01) |
| *A61B 18/00* | (2006.01) |
| *A61B 18/12* | (2006.01) |

(52) U.S. Cl.
CPC  *A61B 18/1477* (2013.01); *A61B 2018/00613* (2013.01); *A61B 2018/124* (2013.01); *A61B 2018/143* (2013.01); *A61B 2018/1432* (2013.01); *A61B 2018/1475* (2013.01)

(58) Field of Classification Search
CPC .......... A61B 18/1477; A61B 2018/143; A61B 2018/1432; A61B 2018/1475; A61B 18/1206; A61B 18/1487; A61B 2017/00867; A61B 2018/00023; A61B 2018/00541; A61B 2018/00547; A61B 2018/00577; A61B 2018/00702; A61B 2018/00791; A61B 2018/1467
USPC ...................................................... 606/32–45
See application file for complete search history.

(56) References Cited

U.S. PATENT DOCUMENTS

| | | | | |
|---|---|---|---|---|
| 5,588,960 A | * | 12/1996 | Edwards ............ | A61B 17/0625 604/20 |
| 5,672,173 A | * | 9/1997 | Gough et al. .................... | 606/41 |
| 5,873,877 A | * | 2/1999 | McGaffigan ....... | A61B 1/00096 606/41 |

(Continued)

FOREIGN PATENT DOCUMENTS

EP         0908156 A1     4/1999

OTHER PUBLICATIONS

PCT International Search Report and Written Opinion for PCT/US2011/024909 mailed Oct. 18, 2011.

*Primary Examiner* — Michael Peffley
*Assistant Examiner* — Amanda Zink
(74) *Attorney, Agent, or Firm* — Zachary F. Madonna (57) ABSTRACT

An energy delivery device for treating a patient includes a probe body; a plurality of guide sleeves positioned inside the probe body and adapted to be deployed radially away from the probe body and into tissue of the patient; and a plurality of elongate electrode elements each adapted to receive electrical treatment energy from an energy source and adapted to be deployed into the tissue through a corresponding deployed guide sleeve. The guide sleeves provide a structural pathway for guiding the electrodes along their intended trajectory and for determining the angle of deployment of the electrodes relative to the longitudinal axis of the probe body.

14 Claims, 12 Drawing Sheets

(56) References Cited

U.S. PATENT DOCUMENTS

| | | | |
|---|---|---|---|
| 6,059,780 A | | 5/2000 | Gough et al. |
| 6,090,105 A | * | 7/2000 | Zepeda et al. .................. 606/41 |
| 6,235,023 B1 | * | 5/2001 | Lee et al. ........................ 606/41 |
| 6,638,275 B1 | * | 10/2003 | McGaffigan ....... A61B 18/1477 606/41 |
| 6,905,480 B2 | * | 6/2005 | McGuckin et al. ..... 604/164.01 |
| 6,958,062 B1 | * | 10/2005 | Gough et al. ................... 606/41 |
| 7,087,040 B2 | * | 8/2006 | McGuckin et al. .......... 604/158 |
| 7,344,533 B2 | * | 3/2008 | Pearson et al. ................. 606/41 |
| 7,449,019 B2 | | 11/2008 | Uchida et al. |
| 8,845,635 B2 | * | 9/2014 | Daniel et al. .................. 606/50 |
| 2006/0089635 A1 | | 4/2006 | Young et al. |
| 2006/0212032 A1 | * | 9/2006 | Daniel et al. .................. 606/41 |
| 2012/0150172 A1 | * | 6/2012 | Ortiz et al. ..................... 606/41 |

* cited by examiner

ABLATION DEVICE WITH GUIDE SLEEVES

CROSS REFERENCE TO RELATED APPLICATIONS

This application claims priority under 35 U.S.C. 119(e) to U.S. Provisional Application No. 61/304,854, filed Feb. 16, 2010, and U.S. Provisional Application No. 61/392,967, filed Oct. 14, 2010, each of which is incorporated herein by reference.

FIELD OF THE INVENTION

The present invention relates to medical devices. More specifically, the present invention relates to a multi-electrode energy delivery device for delivering electrical energy to treat a patient.

BACKGROUND OF THE INVENTION

Irreversible electroporation (IRE) is a new tissue ablation technique in which very high energy electrical pulses are delivered to undesirable tissue to produce cell necrosis. Currently the only commercially available single probe bipolar device for an irreversible electroporation (IRE) procedure is capable of creating a maximum of 1.5 cm ablation. In cases where there is a need for a larger ablation, the user/physician needs to use two or more single probes to perform the ablation. Generally, the size of ablation/tumor will determine the number of probes (at times up to six) that are needed to be used to perform the procedure. These probes need to be closely aligned and tightly spaced to achieve optimal IRE ablation results. The need to place several probes and have them closely aligned can potentially complicate and lengthen the procedure time and consequently the operating room use time required.

Various configurations of antennae as well as electrode probes for ablation of undesired tissue in a patient are known in the art. The term "antennae" and "tines" are known in the art as referring to aspects of radiofrequency (RF) devices and the term "electrode" is known in the art as referring to electrical devices in the context of supraporation (electropurturbation) devices, electroporation (RE) devices and especially in irreversible electroporation (IRE) devices. For convenience and efficiency, in this application, the terms "antennae", "tine" and "electrode" are used interchangeably whether in single or plural form to refer to parts that deliver electrical energy in electrical ablation devices including RF, supraporation, RE and IRE devices.

A detailed explanation of IRE can be found, for example, in U.S. Patent Application Publication Number 2006/0293731, entitled "Methods and systems for treating tumors using electroporation", application Ser. No. 11/165,961 filed on Jun. 24, 2005, which is hereby incorporated by reference. In IRE, electrical pulses in the range of microseconds to milliseconds can be applied to a target tissue zone to produce defects in the cell membrane that are nanoscale in size. The defects in the cell membrane lead to a disruption of homeostasis and eventually cause the cells to die. IRE devices can be designed to be non-thermal and the IRE pulses do not destroy connective and scaffolding structure in the target zone such as nerves and blood vessels.

The IRE pulses are applied using electrical probes, which can be monopolar, bipolar or multi-electrode. The probe designs are similar to the RF probes and accordingly are subject to some of the same problems involving energy distribution along the electrodes.

A single bipolar probe or multi-electrode probe can be used to ablate diseased or unwanted tissue. The positive and negative electrodes are located on a single probe and the tissue is ablated as energy flows from the positive to the negative electrode. Although the bipolar design provides efficient energy deposition in the tissue, the maximum ablation volume is limited and the resulting cylindrical shape of ablation often does not correspond with the targeted tumor shape.

Probes having electrode arrays with an umbrella-like profile achieve larger, more spherical ablations with a single puncture. In this type of probe, two or more outwardly curving tines (electrodes) are placed within the tumor, at predetermined positions, and electrical energy flows between one or more pairs of active tines or electrodes in the array. However, while the array of electrodes in this type of probe is being deployed, the electrodes may lack sufficient strength to adequately pierce through the tissue or may deploy at a wrong angle and can therefore deviate from their intended trajectory. For example, the electrodes may lack sufficient strength to pierce through certain types of more rigid "soft" tissues, such as such as tissues found in the liver, kidneys, lungs, etc. If the electrodes deviate from their intended path and are not ultimately positioned in their predetermined intended locations, treatment of the tissue may not be successful and/or other risks and dangers to the patient may be presented.

SUMMARY OF THE DISCLOSURE

The current device and method provides an energy delivery device for treating a patient. The energy delivery device includes a probe body; a plurality of guide sleeves positioned inside the probe body and adapted to be deployed radially away from the probe body and into tissue of the patient; and a plurality of elongate electrode elements each adapted to receive electrical treatment energy from an energy source and adapted to be deployed into the tissue through a corresponding deployed guide sleeve.

BRIEF DESCRIPTION OF THE DRAWINGS

A more complete understanding of the present device and method can be derived by referring to the detailed description when considered in connection with the following illustrative figures. In the figures like reference numbers refer to like elements or acts throughout the figures. Throughout the specification, the term "distal" is consistently used in reference to the device or portion of the device farthest from the user and "proximal" refers to the end closest to the user of the device.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the current device and method. It will be understood, however, by those skilled in the relevant arts, that the present device and method can be practiced without these specific details. In other instances, known structures and devices are shown or discussed more generally in order to avoid obscuring the present device and method. In many cases, a description of the operation is sufficient to enable one to implement the various forms of the device and method. It should be noted that there are many different and alternative configurations, devices and technologies to which the disclosed device and method can be applied. The full scope of the device and method is not limited to the examples that are described below.

For purpose of this application, the term resistance and impedance have the same meaning and are used interchangeably.

Figure 1:
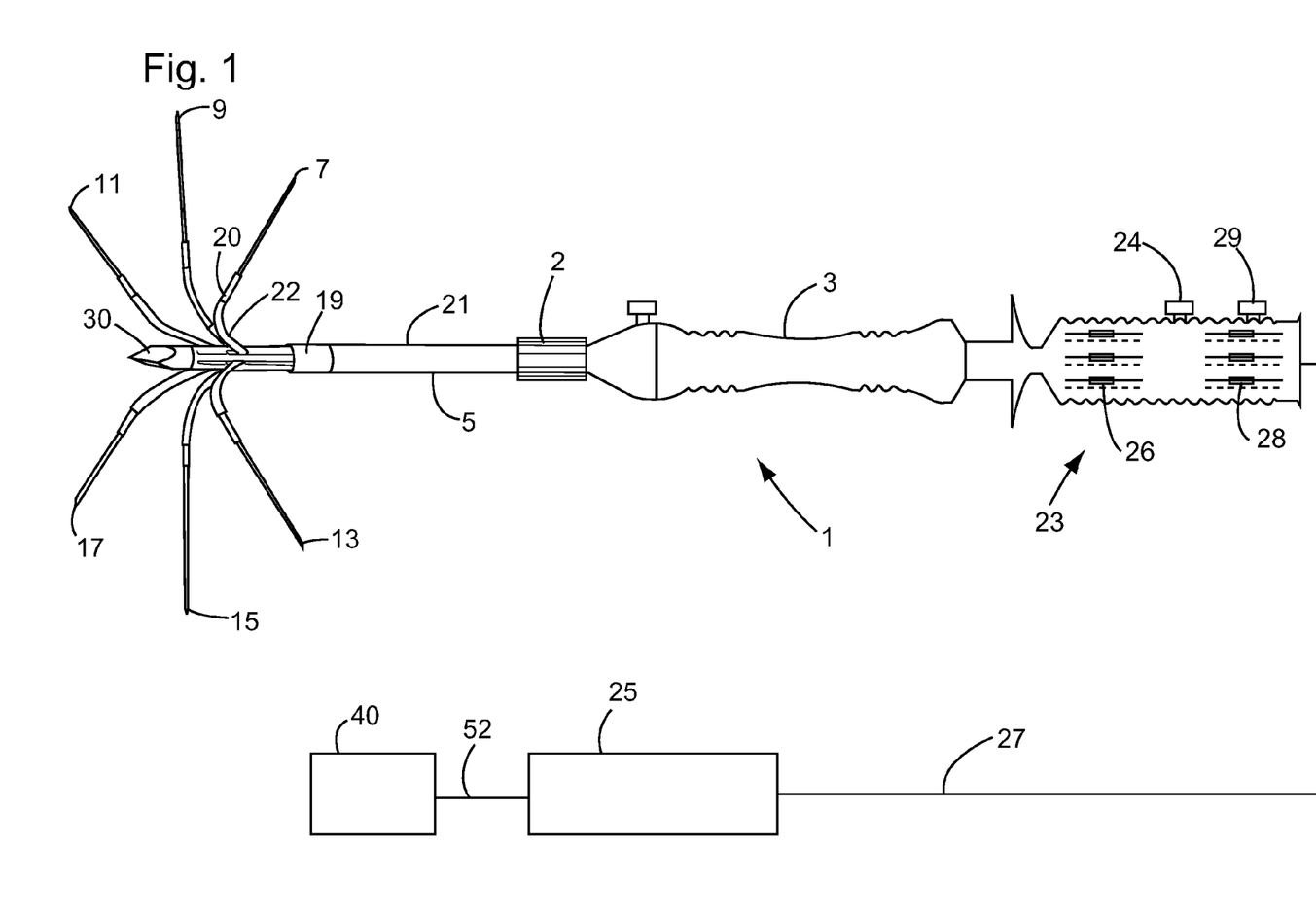
FIG. 1 illustrates a medical treatment system including an energy delivery device with electrodes in a deployed position.

FIG. 1 illustrates a medical treatment system including an energy delivery device 1 with electrodes in a deployed position. The energy delivery device 1 is designed for tissue treatment using electrical treatment signals (i.e., electrical energy such as electrical pulses or alternating current for general or specific purposes such as for electroporative or radiofrequency purposes). The energy delivery device 1 includes a main handle 3, a swivel locking cap 2 attached to the main handle, an elongated probe body 5, an electrode area 19 on the probe body, and a sharp probe tip 30 at the distal end of the probe body 5 for piercing tissue. The probe body is surrounded by insulation material 21, such as any strong, non-conducting polymer (i.e. polyimide). A plurality of guide sleeves 22 are positioned inside the probe body 5 and are adapted to be deployed radially away from the probe body 5 and into tissue of a patient (not shown).

A plurality of curved antenna or electrodes 7,9,11,13,15, 17 are each adapted to receive electrical treatment energy from an energy source and adapted to be deployed into the tissue through a corresponding deployed guide sleeve 22. The device is illustrated in FIG. 1 as including six electrodes. However, the device can have any number of electrodes. The number of electrodes may correspond to the volume of tissue that is to be treated. In one aspect, a distal portion of the probe body 5 includes an electrode area adapted to deliver electrical treatment energy to the tissue. For example, a portion of the sharp probe tip 30 can include an electrode area. The electrodes 7-17 and the electrode area of the sharp probe tip 30 can be made from a conducting material, such as stainless steel or MRI-safe metal, such as INCONEL™ (registered trademark of Special Metals Corporation which refers to a family of austenitic nickel-chromium-based super alloys).

The energy delivery device 1 is designed as a single stick device in which the sharp distal probe tip 30 of the device 1 pierces tissue so as to position the device 1 inside the tissue. The electrodes 7-17 are then deployed radially away from the probe portion 5 through the guide sleeves 22. Each electrode is surrounded by an insulation layer 20, but a distal portion of the electrode is exposed to enable electrical treatment. In one embodiment, the amount of exposure of the distal portion of the electrode is in the range of about 0.5 cm to 1.5 cm.

A first main slide tab 24 on the proximal handle 23 is adapted for a longitudinal sliding movement for controlling the deployment and retraction of the electrodes 7-17 from the elongated probe body 5 and through the guide sleeves 22. In the embodiment shown, the first main slide tab 24 has been fully advanced so as to show the electrodes in their fully deployed position. The energy delivery device 1 includes a deployment mechanism (inside the handle 23) configured to independently control the extent (length) of the deployment of each electrode from the probe 5 using electrode slide tabs 26. Each slide tab 26 controls a corresponding electrode movement independently of other electrodes. As shown in FIG. 1, there are six slide tabs 26 corresponding to the six electrodes 7-17.

The guide sleeves 22 are deployed radially away from the probe body 5 to guide the deployment of the electrodes as will be discussed in more detail later herein. A second main slide tab 29 is adapted for a longitudinal sliding movement for controlling the deployment and retraction of all guide sleeves 20 radially away from the probe body 5 at the same time. The energy delivery device 1 includes a deployment mechanism (inside the handle 23) configured to independently control the extent (length) of the deployment of each guide sleeve 22 from the probe body 5 using guide sleeve slide tabs 28. Each slide tab 28 controls a corresponding movement of a guide sleeve 22. As shown in FIG. 1, there are six guide sleeve slide tabs 28 corresponding to the six guide sleeves 22.

The energy delivery device 1 is designed to apply IRE pulses to treat a patient. For example, the device 1 is designed to generate n sets of m pulses per set with each pulse having a duration of 1 microsecond to 1 millisecond, where n and m=2-20 and the pulse voltage being in the range of 400 volts/cm and 2500 volts/cm.

As shown, the energy delivery device 1 is configured to apply a plurality of pulse sets with each pulse having a pulse duration of 50-150 microseconds and the voltage being 1000 volts/cm to 3000 volts/cm depending on the tissue type being treated. This is more fully described in applicant's application entitled "System and Method for Interactively Planning and Controlling a Treatment of a Patient with a Medical Treatment Device", Ser. No. 12/751,854, filed Mar. 31, 2010, which is incorporated herein in its entirety by reference. Although the present invention is described with reference to IRE pulses, persons of ordinary skill in the art will appreciate that the invention can be applied to any ablation treatment using electrical pulses such as suprapo-ration and radio frequency techniques.

The energy delivery device 1 is coupled to an energy source (e.g., electrical pulse generator) 25 via a cable 27 or other attachment mechanisms known in the art. A user computer 40 is connected to the pulse generator 25 through a communication link 52 and controls the energy source to treat a patient. The cable 27 contains insulated wires that are coupled to the respective electrodes 7-17. The energy source 25 can be capable of releasing energy for purposes of electroporation (including irreversible electroporation) radiofrequency, or other applications. This device can be utilized in applying direct current (DC) or alternating (AC) electrical signals that act on one or more cellular structures including but not limited to internal or external membranes, layers, bi-layers, mitochondria, the nucleus cellular structures within the nucleus, ribosomes, DNA, RNA, reticulum, lysosomes, tubules, vacuoles, as well as application to structures such as proteins and lipids therein.

Figure 2:
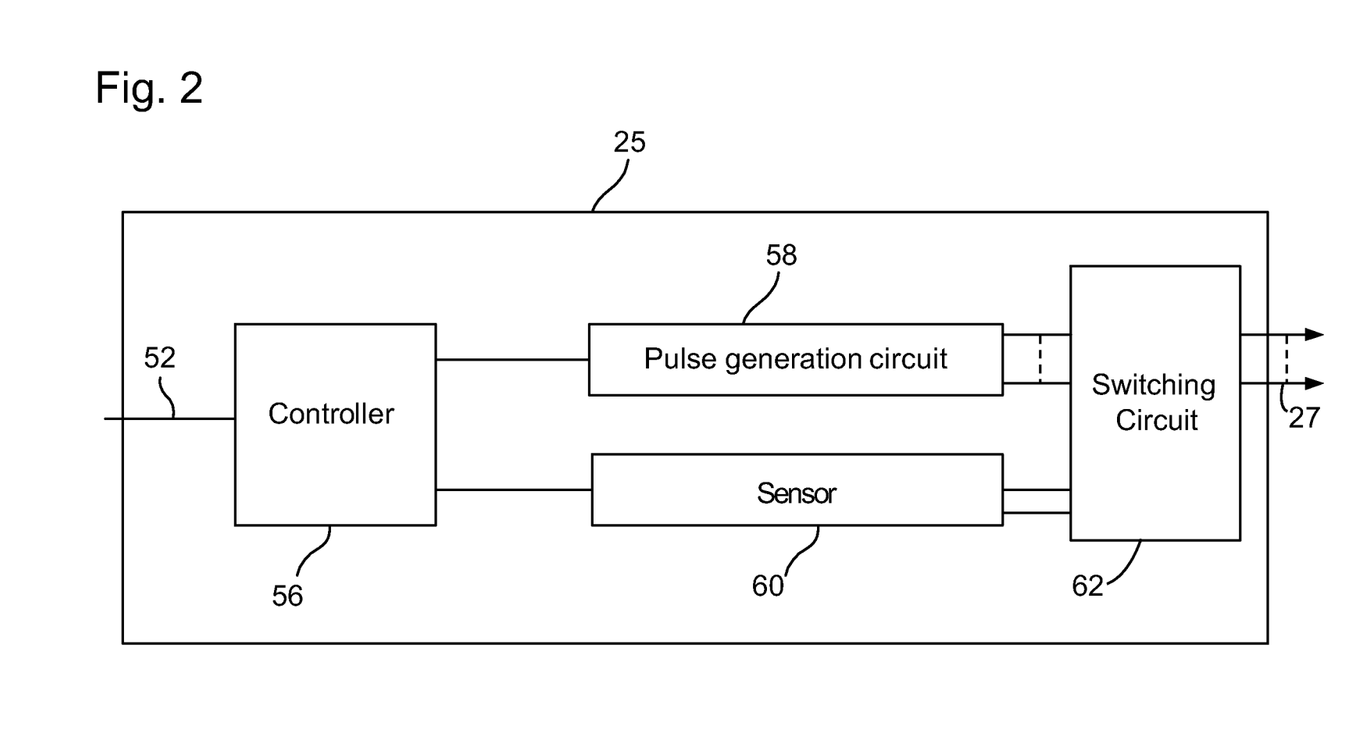
FIG. 2 illustrates a functional block diagram of a pulse generator.

FIG. 2 illustrates a functional block diagram of the pulse generator 25 according to one aspect of the device. A USB (universal serial bus) connection 52 carries instructions from a user computer 40 to a controller 56. The controller 56 can be a computer similar to the computer 40 as shown in FIG. 1. The controller 56 can include a processor, ASIC (application-specific integrated circuit), microcontroller or wired logic. The controller 56 sends the instructions from the user computer 40 to a pulse generation circuit 58. The pulse generation circuit 58 generates the pulses and transmits them to the electrodes 7-17 and 30 through the cable 27. As shown, the pulses are applied one pair of electrodes at a time, and then switched to another pair. A switching circuit 62 is coupled to the controller 56 and switches the electrode pairs based on the instructions received from the computer 40 through the controller. For example, the switching pattern of the electrode pairs can be 30-7, 30-9, 30-11, 30-13, 30-15, and 30-17.

A sensor 60 can sense the resistance (e.g., current and/or voltage) between each pair of the electrodes in real time and communicate such information to the controller 56, which in turn, communicates the information to the computer 40.

Figure 3:
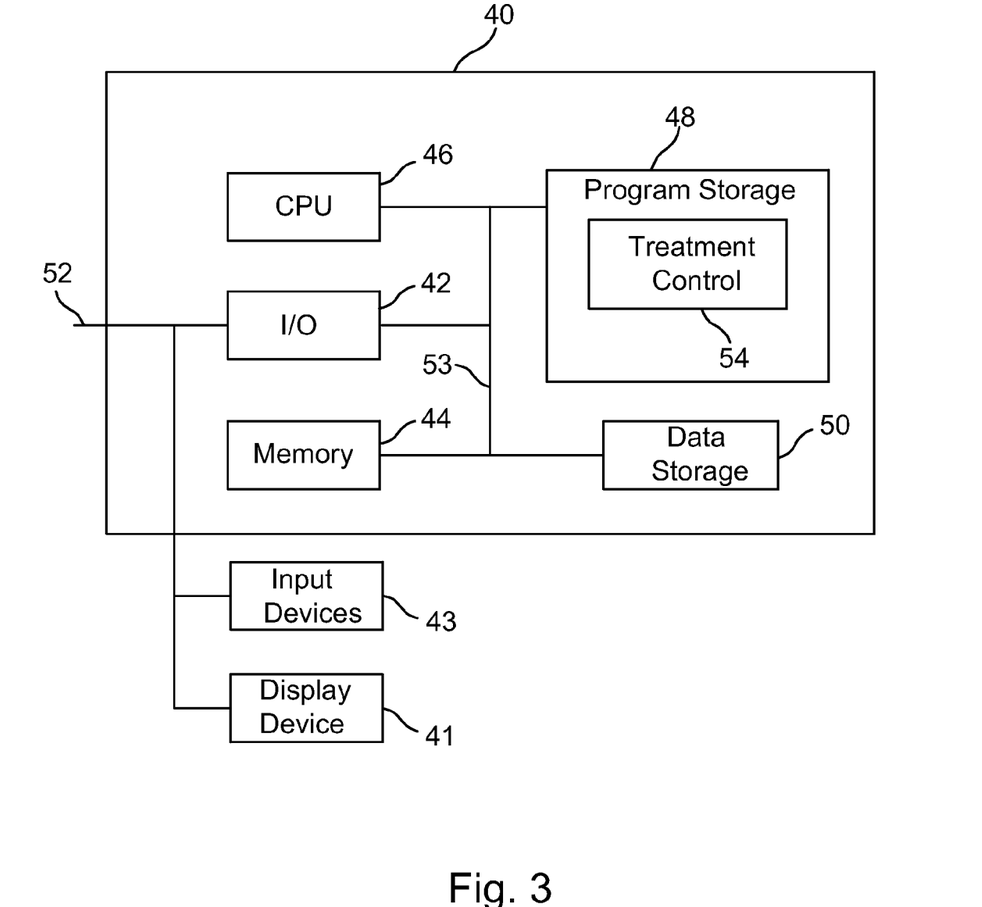
FIG. 3 illustrates a functional block diagram of a user computer for managing treatment for a patient.

Referring now to FIG. 3, the user computer 40 of the present device manages treatment for a patient. The computer 40 is connected to the communication link 52 through an I/O interface 42 such as a USB (universal serial bus) interface, which receives information from and sends information over the communication link 52 to the pulse generator 25. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment. The user interacts with the treatment control module 54 through input devices 43 (e.g., keyboard, mouse, touch screen, trackball and the like) and a display device 41. Any of the software program modules in the program storage 48 and data from the data storage 50 can be transferred to the memory 44 as needed and is executed by the CPU 46.

In one aspect, the computer 40 is built into the voltage generator 25. In another embodiment, the computer 40 is a separate unit which is connected to the voltage generator through the communications link 52. In another aspect, the communication link 52 is a USB link.

Figure 4:
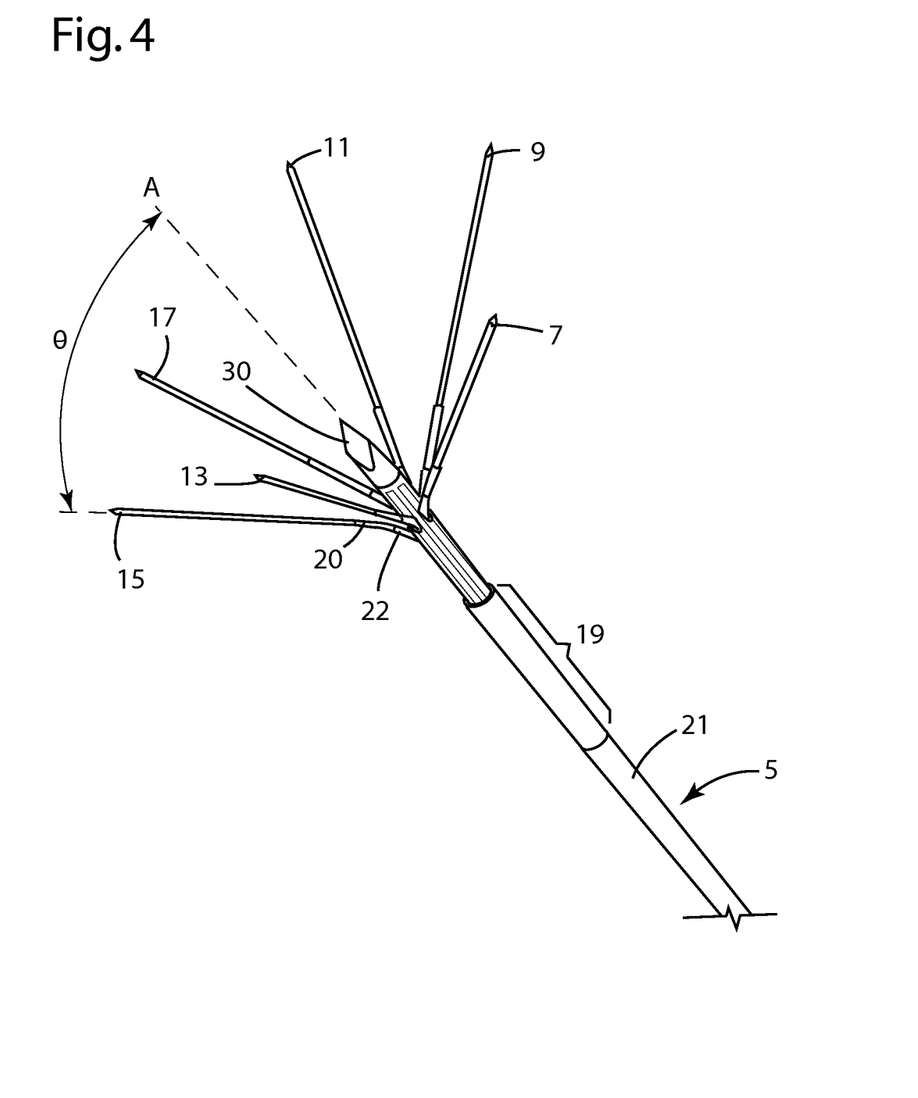
FIGS. 4-6 are perspective views of the distal portion of the energy delivery device of FIG. 1 illustrating deployment of the electrodes at various angles of deployment relative to the longitudinal axis of the probe body.
Figure 5:
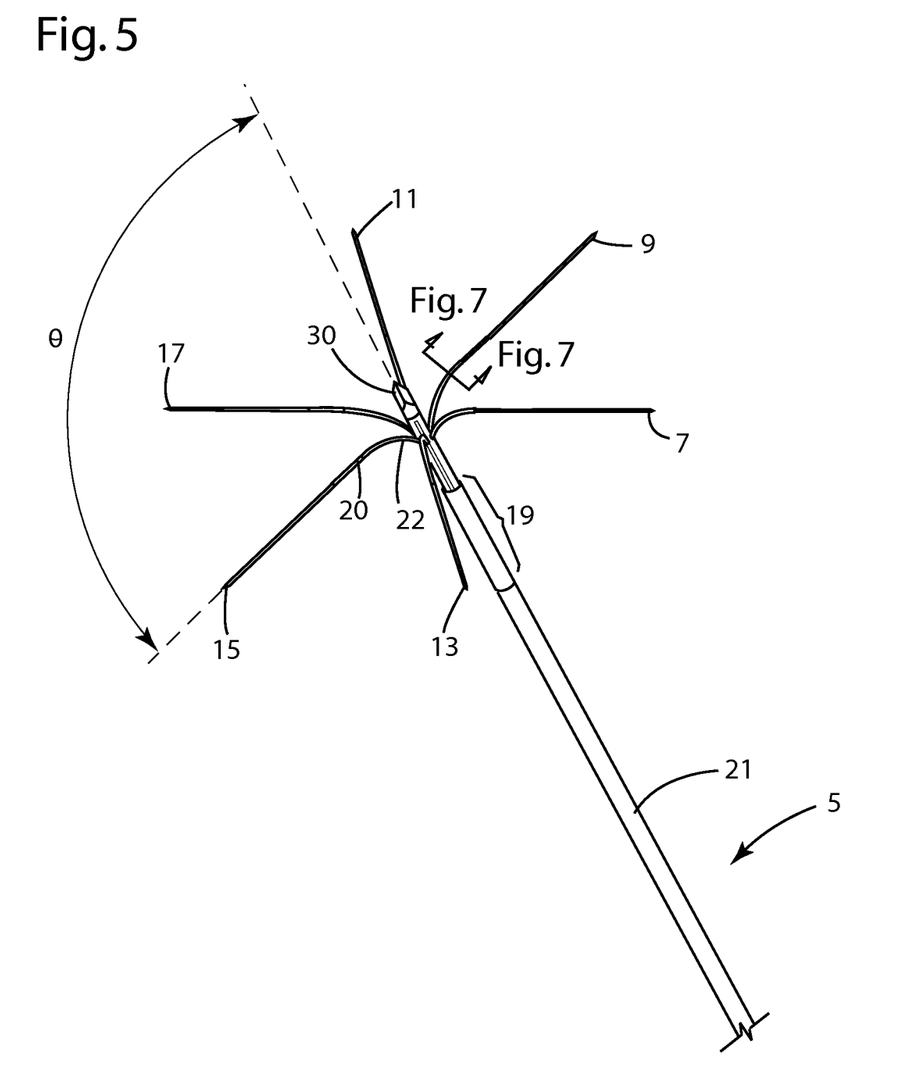
Figure 6:
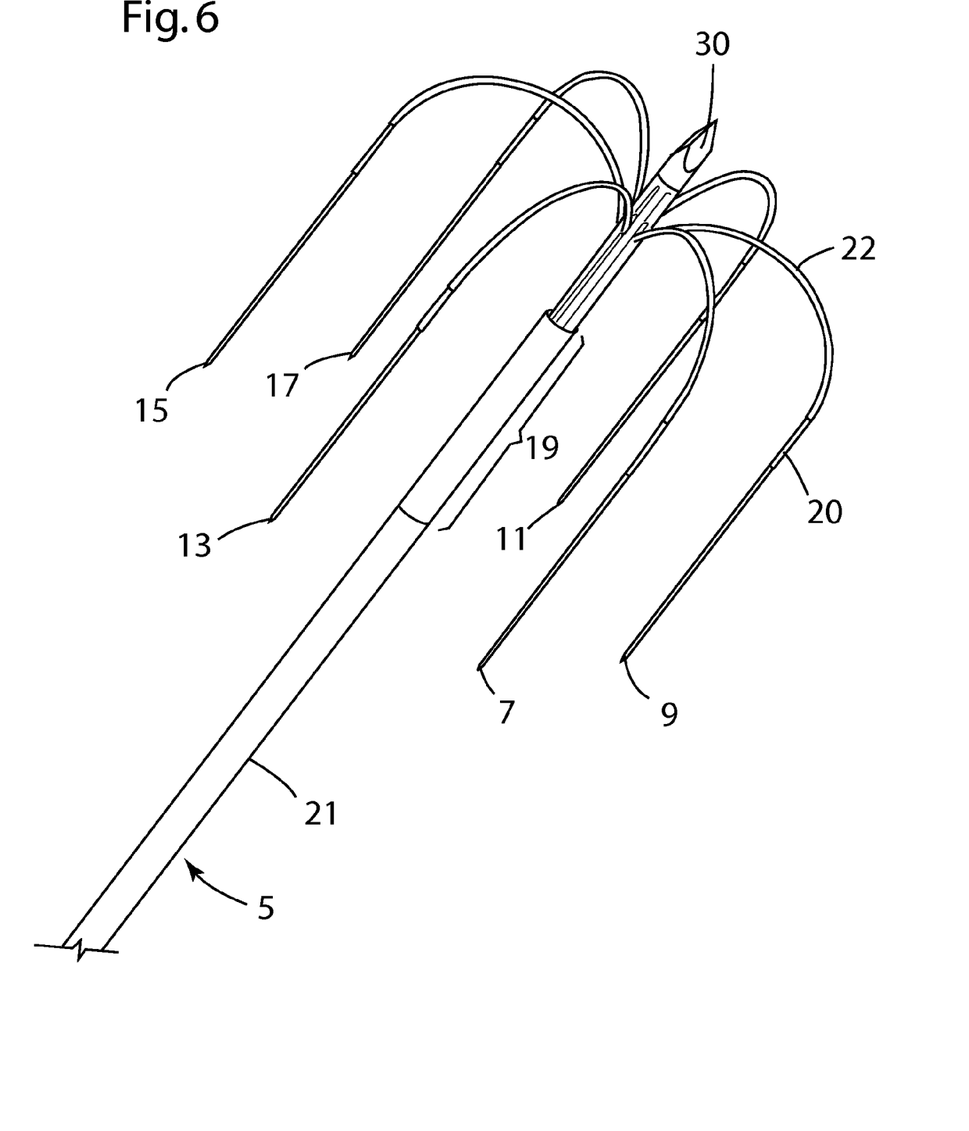

As shown in FIGS. 4-6, the extent of guide sleeve 22 deployment determines the angle of deployment for the corresponding elongate electrode element 7-17 relative to the longitudinal axis A of the probe body 5. FIG. 4 is a perspective view of the distal portion of the energy delivery device of FIG. 1 illustrating deployment of the electrodes 7-17 at approximately a 45 degree angle (θ) of deployment relative to the longitudinal axis A of the probe body 5. FIG. 5 is a perspective view of the distal portion of the energy delivery device of FIG. 1 illustrating deployment of the electrodes 7-17 at approximately a 90 degree angle (θ) of deployment relative to the longitudinal axis A of the probe body 5. FIG. 6 is a perspective view of the distal portion of the energy delivery device of FIG. 1 illustrating deployment of the electrodes 7-17 at approximately a 180 degree angle (θ) of deployment relative to the longitudinal axis A of the probe body 5. As described above, in one embodiment, the extent of deployment of the guide sleeves 22 can be individually controlled for producing a combination of deployment angles for the collection of electrodes. The angle of deployment relative to the longitudinal axis can be any angle in the range of about zero to about 180 degrees from the longitudinal axis A of the probe body 5.

Advantageously, the guide sleeves 22 also ensure that the electrodes are deployed at a predetermined circumferential angle and are uniformly spaced relative to each other. For example, with a six electrode element configuration as shown in FIG. 4, the guide sleeves 22 ensure that the circumferential angle between any two electrode elements is 60 degrees.

The guide sleeves 22 are formed from a material that preferably has a higher strength than the electrodes to thereby pierce tissue and provide a strong pathway for the electrodes to follow during deployment. In one example, the guide sleeves 22 are formed from nickel titanium. In one embodiment, each guide sleeve 22 includes an electrode area adapted to deliver the electrical treatment energy to the tissue.

In one embodiment each guide sleeve 22 is pre-curved and includes a proximal curved portion and a distal straight portion. This configuration will allow for the electrodes to exit the distal portion of the respective guide sleeve and protrude the tissue in a straight and parallel form which is an important requirement for IRE procedure to ensure optimal results. In one embodiment the guide sleeve 22 has a semi-circular pre-curved shape.

In one embodiment, as shown in FIGS. 4-6, an area proximal to the location where the guide sleeves 22 exit the probe body 5 includes an electrode area 19 adapted to deliver the electrical treatment energy to the tissue. This allows another potential pathway for delivering the electrical treatment energy. Thus, ablation electrical pulses can be applied between any two of the following electrode elements or areas: probe tip 30, electrode area 19, electrode elements 7, 9, 11, 13, 15, 17, and electrode areas of guide sleeves 22 to provide maximum flexibility in matching the ablation zone to the target zone.

If the guide sleeves are provided with an electrically active area at its distal portion, then it is possible for such active areas to be in electrical contact with the electrode elements 7-17 when the electrode elements are partially deployed such that the insulation 20 stays well inside the guide sleeves 22. In that case, both the electrically active areas of the guide sleeves 22 and the exposed electrode elements 7-17 which are in electrical contact act as electrodes.

In another embodiment, a portion of each guide sleeve 22 includes an electrode area (not shown) adapted to deliver electrical treatment energy to the tissue. This allows yet another potential pathway for delivering the electrical treatment energy.

Figure 7:
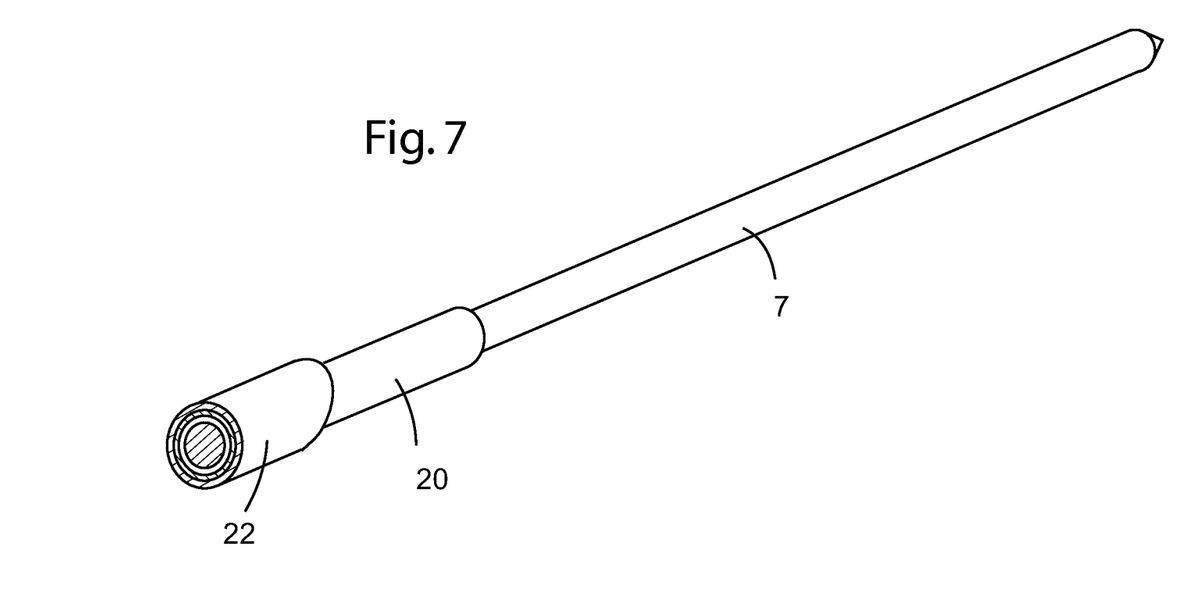
FIG. 7 is a cross-sectional perspective view of the area of the electrode surrounded by a guide sleeve from FIG. 5 along line 7-7.

FIG. 7 is a cross-sectional perspective view of the area of the electrode surrounded by a guide sleeve from FIG. 5 along line 7-7. The electrode 7 is surrounded by a layer of insulation 20 which is non-conductive, such as polyimide. Each guide sleeve 22 surrounds the electrode and has an inner diameter that is larger than the outer diameter of the layer of insulation 20 so that the electrodes can be deployed through each guide sleeve 22 as explained above.

Figure 8:
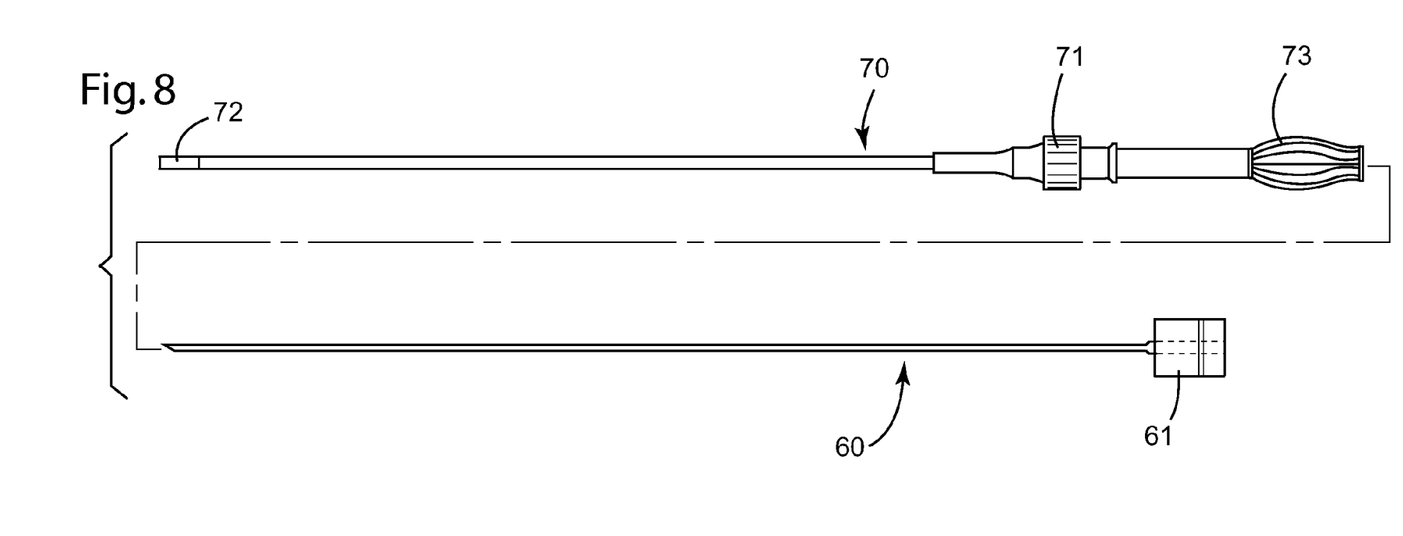
FIG. 8 is an exploded assembly view of an introducer sheath and a corresponding stylet adapted for insertion through the introducer sheath.

FIG. 8 is an exploded assembly view of an introducer sheath 70 and a corresponding stylet 60 adapted for insertion through the introducer sheath 70. The introducer sheath 70 includes an electrode area 72 at its distal end, which is adapted to deliver the electrical treatment energy to the tissue. The introducer sheath 70 includes a proximal electrical connector 73 (i.e. "banana plug" as known in the art) coupled to the electrode area 72 and connectable to an electrical connection located on the probe body (see FIG. 9). The stylet 60 is adapted to be inserted into the introducer sheath 70 and locked thereto by the corresponding locking members 61 and 71, respectively. The stylet 60 includes a sharp distal tip adapted for piercing tissue during insertion of the introducer sheath/stylet assembly.

Figure 9:
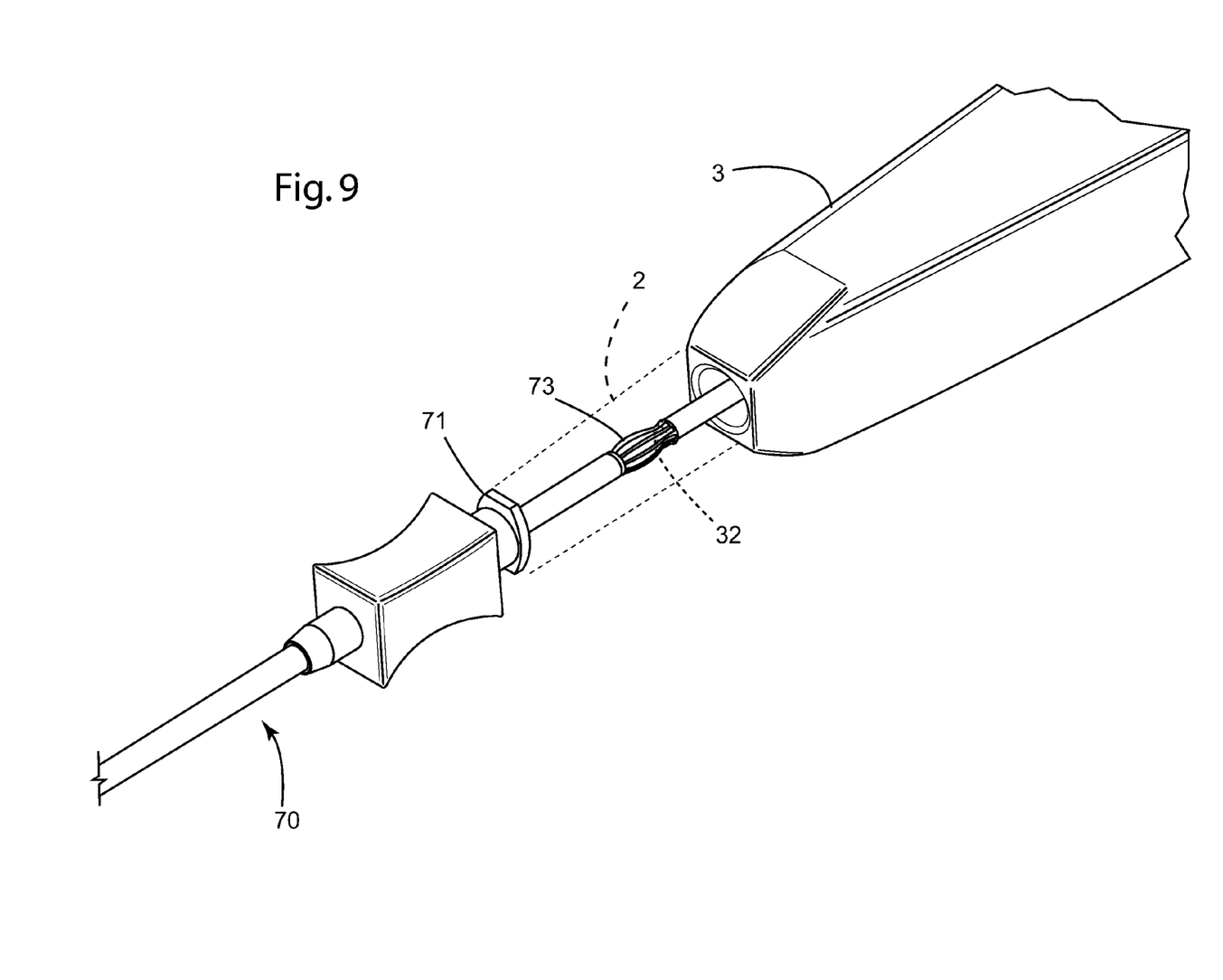
FIG. 9 is a perspective view illustrating the mating of the proximal portion of the introducer sheath of FIG. 8 with the distal portion of the handle of the energy delivery device of FIG. 1.

After the introducer sheath/stylet assembly has been positioned at the treatment site by the physician/user, the corresponding locking members 61 and 71 are unlocked and the stylet 60 is removed and the probe body of the treatment device of FIG. 1 is inserted through the introducer sheath. FIG. 9 is a perspective view illustrating the mating of the proximal portion of the introducer sheath 70 of FIG. 8 with the distal portion of the handle of the energy delivery device of FIG. 1. The swivel locking cap 2 (see also FIG. 1) is connected to the main handle 3 of the energy deliver device and is adapted to mate with the locking member 71 of the introducer sheath 70. In one embodiment, the swivel locking cap 2 includes a threaded inner surface that engages with corresponding threads on the outer surface of the locking member 71. The swivel locking cap 2 can include ridges in its outer surface to assist the user in twisting the locking cap for locking/unlocking. In a locked configuration, the proximal electrical connector 73 of the introducer sheath 70 is connected to an electrical connection 32 located on the probe body for passing electrical treatment energy. As illustrated in the example, this connection can be a frictional engagement between the inner surface of the proximal electrical connector 73 and the outer surface of the electrical connection 32.

Figure 10:
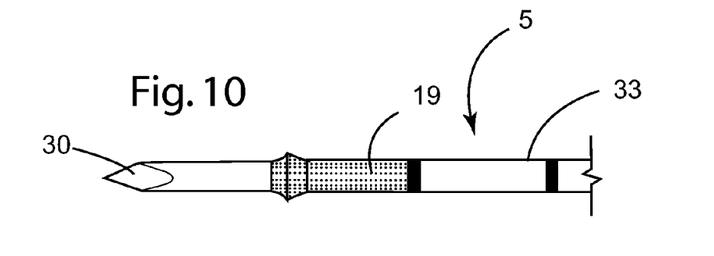
FIGS. 10-12 illustrate side views of an alternative embodiment of an energy delivery device with a retractable outer sleeve.
Figure 11:
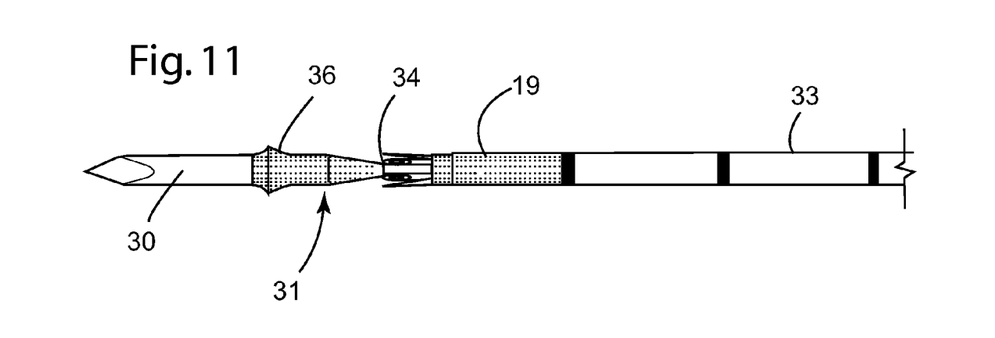
Figure 12:
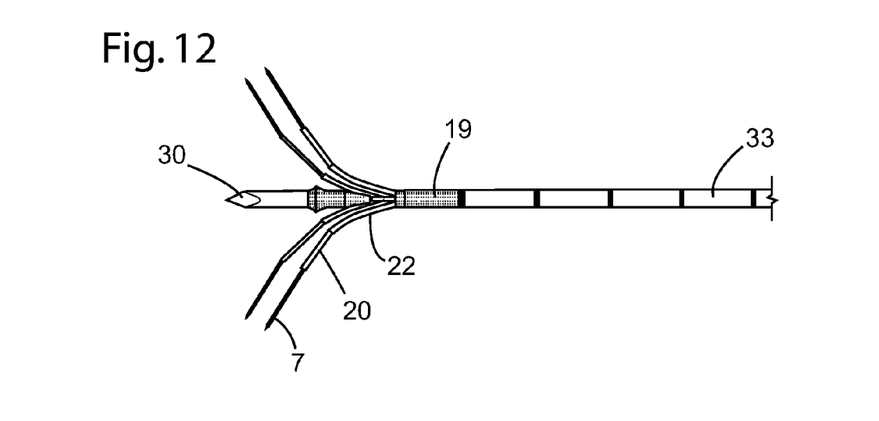

FIGS. 10-12 illustrate side views of an alternative embodiment of an energy delivery device with a retractable outer sleeve 33. A probe tip 30 is attached to a shaft 34 that is disposed inside the probe body 5. The probe tip 30 has a sharp distal end adapted to pierce the tissue. The probe tip 30 has a proximal portion that is adapted to fit within the outer sleeve 33. The probe tip 30 further includes a tapered portion 36 that frictionally engages with the inside surface of the outer sleeve 33 to lock the proximal portion of the probe tip 30 within the distal portion of the probe body 5 in a "closed" position, as shown in FIG. 10. When the probe tip 30 is in the "closed" position, it provides structural strength (lateral and longitudinal strength) during insertion of the probe body 5 into the tissue. The proximal portion of the probe tip 30 in contact with the distal portion of the probe body 5 in the "closed" position can be electrically insulated. The probe body 5 can be further coated with an insulation layer of polyester.

The outer sleeve 33 of the probe body 5 can be mechanically connected to a third main slide tab (not shown) on the proximal handle 23 (see FIG. 1). After the probe body 5 is inserted into the tissue, the outer sleeve 33 of the probe body 5 is retracted into an "open" position via the third main slide tab, as shown in FIG. 11, in which a distal portion of the probe body 5 is longitudinally spaced from the proximal portion of the probe tip 30. The tapered portion 36 is illustrated as having both a tapered leading edge and a tapered trailing edge to allow this portion of the outer surface of the probe tip 30 to become disengaged from the inside surface of the outer sleeve 33, when desired by the physician. In the "open" position, the guide sleeves 22 and/or electrodes 9-17 can be deployed radially away from the probe body 5 and into the tissue, as explained above and as shown in FIG. 12. As explained above, the extent of guide sleeve deployment determines the angle of deployment for the corresponding elongate electrode element relative to the longitudinal axis of the probe body. In one aspect, a distal portion of the probe tip 30 can include an electrode area adapted to deliver the electrical treatment energy to the tissue. In another aspect, the distal portion of the probe body 5 can include an electrode area 19 adapted to deliver the electrical treatment energy to the tissue.

Figure 13:
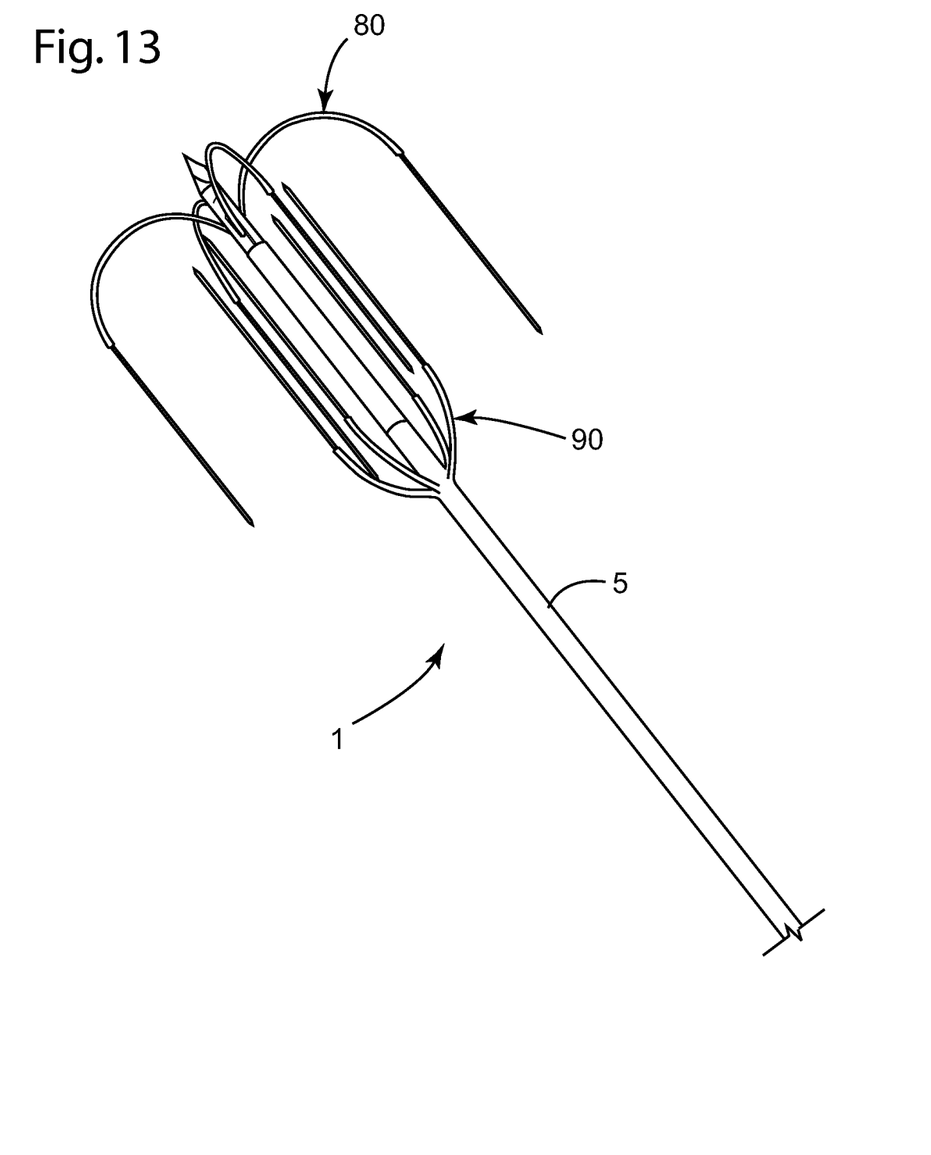
FIGS. 13-14 illustrate a perspective view of alternative embodiments of an energy delivery device having a plurality of first elongate electrode elements which longitudinally overlap with a plurality of second elongate electrode elements.
Figure 14:
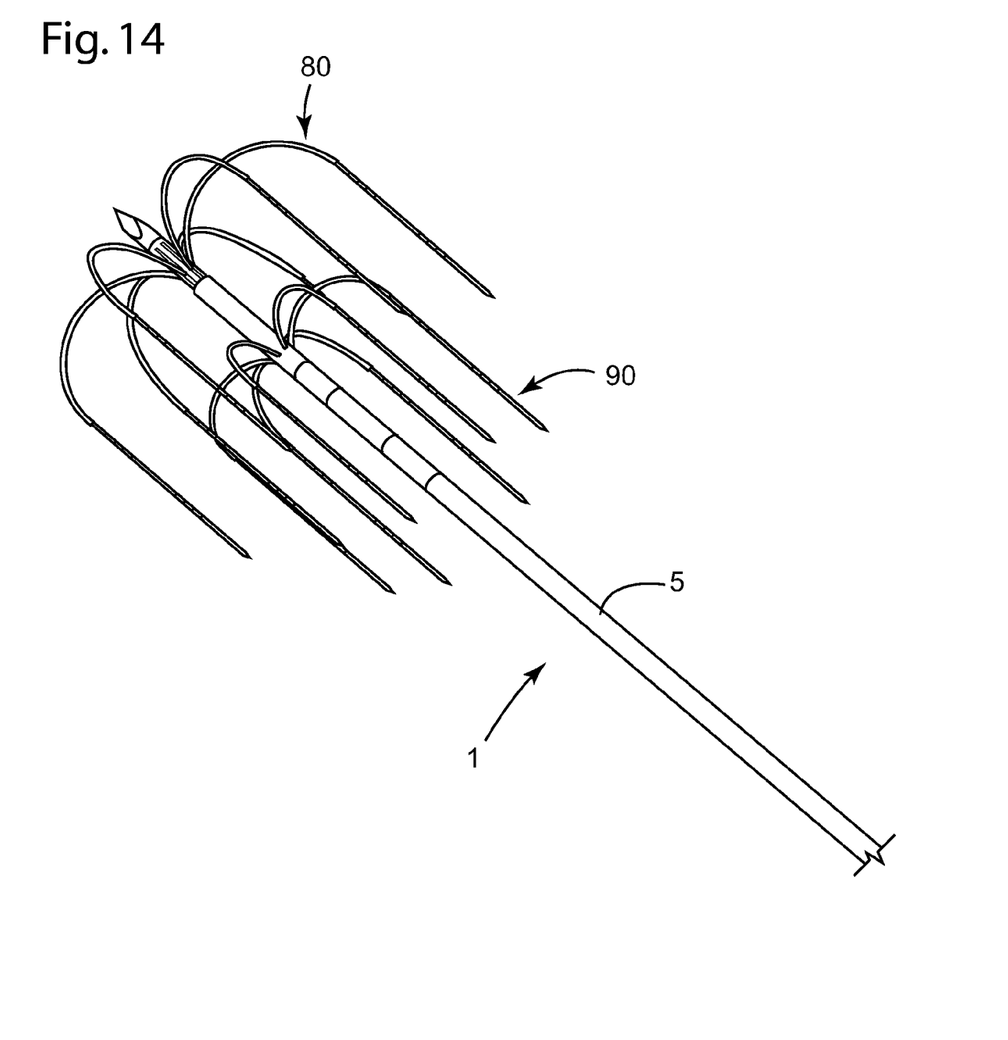

FIGS. 13-14 illustrate a perspective view of alternative embodiments of an energy delivery device having a plurality of first elongate electrode elements which longitudinally overlap with a plurality of second elongate electrode elements.

FIG. 13 shows an alternative embodiment wherein the energy delivery device 1 includes a plurality of second elongate electrode elements 90 positioned proximally of the plurality of first elongate electrode elements 80 (as described as elements 7-17 with reference to FIG. 1) and adapted to be deployed radially away from the probe body 5 and into the tissue such that the deployed first electrode elements 80 longitudinally overlap with the deployed second electrode elements 90. In the embodiment shown in FIG. 13, viewing the probe body 5 from the probe tip 30, the electrode elements 80 deploy in a convex manner while the second electrode elements 90 deploy in a concave manner. This embodiment can make it possible to create a larger area of ablation. The longitudinal spacing between the first and second electrode elements can vary by design based on the treatment requirements.

FIG. 14 shows an alternative embodiment wherein the energy delivery device 1 includes a plurality of second elongate electrode elements 90 positioned proximally of the plurality of first elongate electrode elements 80 (as described with reference to FIG. 1) and adapted to be deployed distally and radially away from the probe body 5 and into the tissue such that the deployed first electrode elements 80 longitudinally overlap with the deployed second electrode elements 90. In this embodiment, both sets of electrode elements deploy in a convex manner. This embodiment can make it possible to create a larger area of ablation. In one aspect, a two tier design is achieved wherein the first elongate electrode elements 80 create a larger tier and the second elongate electrode elements 90 create a smaller tier "nested" within the larger tier. The longitudinal spacing between the first and second electrode elements and the relative sizes of the tiers can vary by design based on the treatment requirements.

A method of treating a patient using the energy delivery device 1 of the present invention will now be described. Prior to inserting the device into the tissue, certain procedures are performed. Specifically, the physician identifies a target tissue zone to be ablated in a patient and selects an appropriate multi-electrode probe for the treatment (e.g., probe with 6 electrodes).

An introducer sheath 70 (see FIG. 8) can be inserted into the tissue as an optional first step, wherein the introducer sheath 70 can include an electrode area 72 adapted to deliver electrical treatment energy to the tissue. Then, the selected probe body 5 is inserted through the introducer sheath 70, if used, and into the identified tissue zone by piercing the tissue with the sharp end of the probe body 5. If the introducer sheath 70 is used, then the proximal electrical connector 73 (see FIG. 9) is coupled to the electrode area 72 by connecting the proximal electrical connector 73 to an electrical connection 32 located on the probe body.

Once the probe body 5 is inserted, the physician deploys the plurality of guide sleeves 22 positioned inside the probe body 5 radially away from the probe body 5 and into the tissue. As described above, the guide sleeves 22 can be pre-curved and the amount of deployment of each guide sleeve can be selected to establish the angle of deployment for the elongate electrode elements relative to the longitudinal axis of the probe body 5 (see FIGS. 4-6). Next, the physician deploys the plurality of elongate electrode elements 7-17 through the deployed guide sleeves 22 using the deployed guide sleeves 22 as a guide. Next, electrical treatment is delivered to the tissue.

In an alternative embodiment, if the treatment method includes the device described in FIGS. 10-12 above, then the step of inserting the probe body includes: inserting the probe body with the probe tip 30 in the "closed" position; and moving the probe tip 30 to the "open" position for deployment of the plurality of elongate electrode elements.

The apparatus and method disclosed herein can be used in laparoscopic, percutaneous, natural orifice procedures (NOTES), as well as open surgical procedures as well as when the target tissue either actually is one of the following tissues or is within the following tissues: digestive, skeletal, muscular, nervous, endocrine, circulatory, reproductive, integumentary, lymphatic, urinary, and soft tissue. The method can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, or tumorous.

The apparatus and method disclosed herein can be used with various treatment modalities including radiofrequency, reversible electroporation, irreversible electroporation, and supraporation.

The above disclosure is intended to be illustrative and not exhaustive. This description will suggest many modifications, variations, and alternatives may be made by ordinary skill in this art without departing from the scope of the device and method. Those familiar with the art may recognize other equivalents to the specific embodiments described herein. Accordingly, the scope of the device and method described herein is not limited to the foregoing specification.

What is claimed is:

1. An energy delivery device for treating a patient by electroporation (EP) comprising:
   a probe body having a plurality of circumferentially arranged openings at a predetermined distance from a distal end of the probe body;
   at least three guide sleeves positioned inside the probe body and adapted to be deployed outside of the probe body through a respective opening and into tissue of the patient, the at least three guide sleeves being adapted to deploy at predetermined circumferential angles and uniformly spaced relative to each other such that the circumferential angle between any two of the at least three adjacent deployed guide sleeves is substantially the same; and
   a plurality of elongate electrode elements, each having an outer layer comprised of an insulative material, each elongate electrode element adapted to receive EP pulses as electrical treatment energy from an energy source and adapted to be deployed into the tissue through a corresponding deployed guide sleeve.

2. The energy delivery device of claim 1, wherein the at least three guide sleeves are pre-curved guide sleeves wherein the extent of sleeve deployment determines the angle of deployment for the corresponding elongate electrode element relative to the longitudinal axis of the probe body and the extent of guide sleeve deployment is selectable by a user.

3. The energy delivery device of claim 2, wherein each pre-curved guide sleeve has a proximal curved portion and a distal straight portion.

4. The energy delivery device of claim 2, wherein each pre-curved guide sleeve is sufficiently curved to allow the corresponding elongate electrode element to be deployed at an angle greater than 90 degrees relative to the longitudinal axis of the probe body.

5. The energy delivery device of claim 1, wherein each of the at least three guide sleeves includes an electrode area adapted to deliver the electrical treatment energy to the tissue.

6. The energy delivery device of claim 1, wherein a distal portion of the probe body includes an electrode area adapted to deliver the electrical treatment energy to the tissue.

7. The energy delivery device of claim 1, wherein an area proximal to the location where the guide sleeves exit the probe body includes an electrode area adapted to deliver the electrical treatment energy to the tissue.

8. The energy delivery device of claim 1, further comprising an introducer sheath through which the probe body is inserted and including an electrode area adapted to deliver the electrical treatment energy to the tissue.

9. The energy delivery device of claim 1, further comprising:
   a shaft disposed inside the probe body;
   a probe tip attached to the shaft for movement between an open position in which a distal portion of the probe body is longitudinally spaced from a proximal portion of the probe tip, and a closed position in which the distal portion of the probe body slides over the proximal portion of the probe tip to provide structural strength during insertion of the probe body into the tissue.

10. A method of treating a patient by electroporation (EP) comprising:
   inserting a probe body of an energy delivery device into tissue of the patient, the probe body having a plurality of circumferentially arranged openings at a predetermined distance from a distal end of the probe body;
   deploying at least three guide sleeves positioned inside the probe body outside of the probe body through a respective opening and into the tissue, the at least three guide sleeves being adapted to deploy at predetermined circumferential angles and uniformly spaced relative to each other such that the circumferential angle between any two of the at least three adjacent deployed guide sleeves is substantially the same;
   deploying a plurality of elongate electrode elements through the at least three deployed guide sleeves using the at least three deployed guide sleeves as a guide, each of the plurality of elongate electrode elements having an insulation layer adapted to be deployed through the guide sleeves; and delivering EP pulses as electrical treatment energy to the tissue through the deployed electrodes.

11. The method of claim 10, wherein the at least three guide sleeves are pre-curved and the step of deploying the at least three guide sleeves includes deploying the at least three guide sleeves for a selected amount to establish the angle of deployment for the elongate electrode elements relative to the longitudinal axis of the probe body.

12. The method of claim 10, prior to the step of inserting a probe body, further comprising:
 inserting, into the tissue, an introducer sheath having an electrode area adapted to deliver the electrical treatment energy to the tissue.

13. The method of claim 12, wherein the introducer sheath includes a proximal electrical connector coupled to the electrode area and the method further comprises connecting the proximal electrical connector to an electrical connection located on the probe body.

14. The method of claim 10, wherein the energy delivery device includes:
 a shaft disposed inside the probe body; and
 a probe tip attached to the shaft for movement between an open position in which a distal portion of the probe body is longitudinally spaced from a proximal portion of the probe tip, and a closed position in which the distal portion of the probe body slides over the proximal portion of the probe tip, wherein:
 the step of inserting a probe body includes:
 inserting the probe body with the probe tip in the closed position;
 moving the probe tip to the open position for deployment of the plurality of elongate electrode elements.

* * * * *